United States Patent [19]

Fehr

[11] 4,429,139

[45] Jan. 31, 1984

[54] PROCESS FOR THE PREPARATION OF ROSE OXIDE

[75] Inventor: Charles Fehr, Versoix, Switzerland

[73] Assignee: Firmenich SA, Geneva, Switzerland

[21] Appl. No.: 435,314

[22] Filed: Oct. 19, 1982

[30] Foreign Application Priority Data

Nov. 4, 1981 [CH] Switzerland ................. 7042/81

[51] Int. Cl.$^3$ ............................................ C07D 309/04
[52] U.S. Cl. ................................. 549/356; 568/857; 568/46; 568/37
[58] Field of Search ..................... 549/356; 568/857

[56] References Cited

U.S. PATENT DOCUMENTS

| | | |
|---|---|---|
| 3,161,657 | 12/1964 | Eschenmoser et al. ........... 549/356 |
| 3,163,658 | 12/1964 | Eschinasi et al. ................. 549/356 |
| 3,166,575 | 1/1965 | Naves et al. ...................... 549/356 |
| 3,166,576 | 1/1965 | Markus ............................. 549/356 |
| 3,252,998 | 5/1966 | Ohloff et al. ..................... 549/356 |
| 3,328,426 | 6/1967 | Ohloff .............................. 549/356 |
| 3,657,278 | 4/1972 | Böse et al. ........................ 549/356 |
| 4,340,544 | 7/1982 | Suzukamo et al. ............... 549/356 |

*Primary Examiner*—Nicky Chan
*Attorney, Agent, or Firm*—Pennie & Edmonds

[57] ABSTRACT

Rose oxide, or 2-[2-methyl-prop-1-en-1-yl]-4-methyl-tetrahydropyrane, a fragrant chemical specialty, is prepared efficiently by a novel process which consists in five reaction steps and uses citronellol as starting material.

4 Claims, No Drawings

PROCESS FOR THE PREPARATION OF ROSE OXIDE

BRIEF SUMMARY OF THE INVENTION

Rose oxide is prepared by a process which comprises the following reaction steps:

a. an epoxidation of citronellol to give 3,7-dimethyl-6,7-epoxy-1-octanol;
b. a treatment of the obtained mixture with thiophenol to give 3,7-dimethyl-6-phenylthio-1,7-octanediol;
c. an oxidation of the obtained product to give the corresponding sulfoxide;
d. a thermal treatment of 3,7-dimethyl-6-phenylsulfinyl-1,7-octanediol thus obtained at a temperature of between about 300° and 400° C., and
e. a treatment of the reaction mixture thus formed with an acidic cyclizing agent.

BACKGROUND OF THE INVENTION

Rose oxide, or 2-[2-methyl-prop-1-en-1-yl]-4-methyl-tetrahydropyrane, of formula

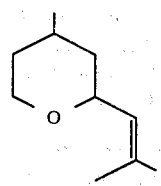

is a compound of special renown in the fragrance industry. Since its discovery in 1960 [see Swiss Pat. No. 395,406], numerous scientific publications have related to new syntheses for its preparation. A synthetic approach, starting from 3-methyl-but-2-en-1-al and 2-methyl-but-1-en-4-ol, was suggested by J. P. H. Tyman and B. J. Willis [cf. Tetrahedron Letters, 51, 4507 (1970)] and by Firmenich [see G.B. Pat. No. 2,036,004].

The present invention relates to a new process for the preparation of rose oxide, which process makes use of cheap commercially available starting materials and enables the preparation of the desired product in good yields.

THE INVENTION

The said process of the invention can be illustrated by the following reaction scheme:

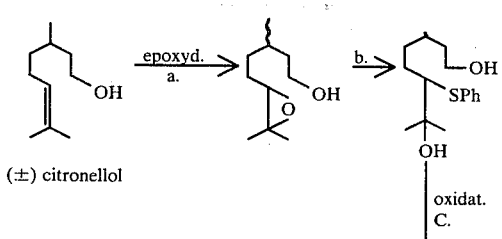

(±) citronellol

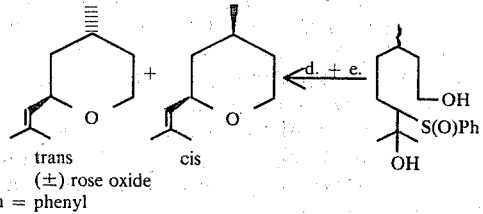

trans    cis
(±) rose oxide
Ph = phenyl

Of course the process illustrated above for (±) citronellol can be applied without difficulty to each one of its optically active antipodes, namely to (−) citronellol to give (−) rose oxide, a product which possesses a sweeter, fresher and more elegant fragrance character than that of its racemic derivative.

Each of the separate steps of the process illustrated above represents a reaction of known type, the originality of the process resides however in the particular choice of the reaction sequence and of the reactants used.

Step a, which consists in the epoxidation of the double bond of citronellol, can be effected by means of peracid, preferably in an inert organic solvent. Suitable peracids include peracetic acid in a chlorinated hydrocarbon such as dichloromethylene.

The reaction with thiophenol is carried out in an inert organic solvent such as an aromatic hydrocarbon, optionally in admixture with a polar solvent, e.g. dimethylformamide, and in the presence of a stoichiometric amount of sodium or potassium carbonate.

The reaction, which is preferably effected at a temperature in the vicinity of the boiling temperature of the chosen solvent or mixture of solvents, enables the almost theoretical conversion of citronellol epoxide into its corresponding thioether which, after oxidation to give the desired sulfoxide by means for instance of hydrogen peroxide, is subjected to a thermal treatment in the presence of a base.

The said thermolysis enables to obtain a mixture which, by treatment with an acidic cyclizing agent, gives the desired rose oxide.

Such a reaction sequence is particularly advantageous as the end product is obtained with excellent yield. We have observed that by carrying out the thermolysis in the absence of a basic agent, it was possible to obtain directly mixtures wherein rose oxide was accompanied by various amounts of the isomeric compound 2-[2-methyl-prop-2-en-1-yl]-4-methyl-tetrahydropyrane.

The product obtained directly by the thermolysis in the presence of a basic agent consists in a mixture comprising eminently the diol of formula

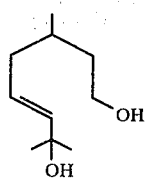

which compound can then be converted into rose oxide by cyclization with an acidic cyclizing agent. Suitable cyclizing agent include a mineral protonic acid or a Lewis type acid, e.g. BF$_3$.

The thermal treatment according to step d. of the disclosed process can be effected at temperatures varying within a wide range; we have observed that the best yield were obtained at temperatures of between about 300° and 400° C. As indicated above, the thermal treatment can optionally be effected in the presence of a base, for instance in the presence of a tertiary amine such as triethylamine. Though less effective, other basic agents, such as sodium carbonate, can also be used.

The following example can illustrate the invention in a more detailed manner. The temperatures are indicated in degrees centigrade and the abbreviations have the meaning common in the art.

EXAMPLE a. 3,7-Dimethyl-6,7-epoxy-1-octanol 210 g (1.1 M) of 40% peracetic acid were added dropwise within 1 h to a stirred suspension of 156 g (0.95 M; purity 95%) of citronellol kept at 0° and 53 g (0.5 M) of sodium carbonate in 200 ml of toluene. The reaction mixture was kept under stirring at 20° during 4 h then it was washed with water, a 5% solution of sodium sulfite and a 10% aqueous solution of $NaHCO_3$. After drying over anhydrous sodium sulfate, evaporation of the solvent and distillation (70°–78°/20 × $10^2$ Pa), 139 g (yield 83%; purity 98%) of the desired epoxide were obtained.

b. 3,7-Dimethyl-6-phenylthio-1,7-octanediol

A suspension of 82 g (0.47 M) of the epoxide obtained under letter a. above, 65 g (0.47 M) of potassium carbonate, 52 g (0.47 M) of thiophenol, 240 ml of toluene and 12 ml of dimethyl-formamide was refluxed during 8 h. After addition of water, the organic phase was separated and washed successively with water and with brine, whereupon it was dried over sodium sulfate and evaporated. The obtained raw material (145 g; yield about 100%) was utilized for the subsequent reaction step without prior purification.

A purified sample obtained by elution with a 9:1 mixture of cyclohexane/ethyl acetate on a $SiO_2$ filled column possessed the following analytical characteristics:

IR (film): 3400, 2940, 1585, 1480, 1440, 1380 $cm^{-1}$;
NMR (60 MHz, $CDCl_3$): 0.93 (3H, m); 1.24 (3H, s); 1.33 (3H, s) 1.30–2.20 (8H, m); 2.70–3.20 (2H, m); 3.60 (2H, m); 7.15–7.60 (5H, m) δppm;
MS: 92(76), 91(100), 65(14).

c. 3,7-Dimethyl-6-phenylsulfinyl-1,7-octanediol 85 g (1.42 M) of acetic acid and 34 g (0.70 M) of 70% hydrogen peroxide were successively added dropwise within 20 minutes to a stirred solution kept at 0° of 145 g of the phenylthio-ether obtained sub. letter b above. The reaction mixture was kept under stirring for 15 h at +5°, then it was washed successively with water, a 10% aqueous solution of $NaHCO_3$, dried over sodium sulfate and concentrated under reduced pressure (13.3–0.133 × $10^2$ Pa). 148 g of the desired sulfoxide were thus obtained with a yield of about 100%.

An analytical sample was purified by column chromatography ($SiO_2$; eluant: 9/1 cyclohexane/ethyl acetate).

IR (film): 3400, 2930, 1445, 1380 $cm^{-1}$;
NMR ($CDCl_3$): 0.69 (3H, m); 1.00–1.60 (15H); 2.84 (1H, m); 3.43 (2H, m); 7.42–7.97 (5H, m) δppm;
MS: 298(100), 223(29), 173(43), 155(63), 137(91), 126(81), 109(55), 95(69), 81(87), 69(79), 55(81).

d. 3,7-Dimethyl-oct-5-en-1,7-diol

A solution of 12.0 g (38.2 M) of the sulfoxide obtained sub letter c. above in 12 g of toluene and 4 g of triethylamine was introduced at one end of a quartz column of 3.5 m length heated at 350° and then put under vacuum at 26.6 × $10^2$ Pa. The introduction is effected by means of a needle of 15 cm length. The product formed after thermolysis was collected in a trap cooled at −10°.

e. Rose oxide

The crude mixture obtained was evaporated under reduced pressure, treated with 1 g of potassium bisulfate and distilled with a Vigreux column (10 cm) to give 4.46 g of an isomeric mixture of rose oxide (yield 73%). The mixture was constituted by about 2 parts of the cis isomer and about 1 part of the trans isomer. The analytical characteristics of the obtained product were identical in all respects to those of a control sample.

What I claim is:

1. A process for the preparation of rose oxide which comprises the following reaction steps:
   a. an epoxidation of citronellol to give 3,7-dimethyl 6,7-epoxy-1-octanol;
   b. a treatment of the obtained mixture with thiophenol to give 3,7-dimethyl-6-phenylthio-1,7-octanediol;
   c. an oxidation of the obtained product to give the corresponding sulfoxide;
   d. a thermal treatment of 3,7-dimethyl-6-phenylsulfinyl-1,7-octanediol thus obtained at a temperature of between about 300° and 400° C., and
   e. a treatment of the reaction mixture thus formed with an acidic cyclizing agent.

2. A process according to claim 1, wherein the epoxidation of step a. is effected by means of peracetic acid.

3. A process according to claim 1, wherein the thermal treatment of 3,7-dimethyl-6-phenylsulfinyl-1,7-octanediol is carried out at subatmospheric pressure in the presence of toluene and of a basic agent.

4. A process according to claim 1, wherein (−) citronellol is used as starting material to give a cis/trans mixture of (−) 2-[2-methylprop-1-en-1-yl]-4-methyl-tetrahydropyrane.

* * * * *